United States Patent
Otani et al.

(10) Patent No.: US 7,557,913 B2
(45) Date of Patent: Jul. 7, 2009

(54) OPTICAL APPARATUS FOR DEFECT INSPECTION

(75) Inventors: Seiji Otani, Hadano (JP); Koichi Nagoya, Konosu (JP)

(73) Assignee: Hitachi High-Technologies Coropration, Tokyo (JP)

( * ) Notice: Subject to any disclaimer, the term of this patent is extended or adjusted under 35 U.S.C. 154(b) by 189 days.

(21) Appl. No.: 11/822,003

(22) Filed: Jun. 29, 2007

(65) Prior Publication Data
US 2008/0002195 A1    Jan. 3, 2008

(30) Foreign Application Priority Data
Jun. 30, 2006    (JP) .............................. 2006-180639

(51) Int. Cl.
*G01N 21/88*    (2006.01)
(52) U.S. Cl. ............................... 356/237.3; 356/237.5
(58) Field of Classification Search ... 356/237.1–237.5; 250/559.41, 559.04, 559.45
See application file for complete search history.

(56) References Cited

U.S. PATENT DOCUMENTS 6,797,975 B2 *    9/2004    Nishiyama et al. ..... 250/559.04
6,888,959 B2 *    5/2005    Hamamatsu et al. ........ 382/149
6,936,835 B2 *    8/2005    Nishiyama et al. ..... 250/559.41
7,474,394 B2 *    1/2009    Hamamatsu et al. ..... 356/237.2
2009/0027664 A1 *    1/2009    Hamamatsu et al. ..... 356/237.5

FOREIGN PATENT DOCUMENTS

JP    62-89336    4/1987

* cited by examiner

*Primary Examiner*—Hoa Q Pham
(74) *Attorney, Agent, or Firm*—McDermott Will & Emery LLP (57) ABSTRACT

An optical apparatus for defect inspection having an illuminating optical system for irradiating illumination light beams on the surface of a specimen to form a beam spot and a detection optical system for detecting a reflection light ray originating from the beam spot comprises a storage unit in which the position and size of a standard particle of known size on a specimen for correction are stored in advance, a correction processing section which, when the correction specimen is used as an inspection target, correlates a detected scattering light quantity from the standard particle with the known size of standard particle stored at a corresponding position in the storage unit to prepare a correlation between the scattering light quantity and a true value, and a signal processing section which, when an inspection wafer is used as an inspection target, converts a detected scattering light quantity into a defect dimension.

5 Claims, 11 Drawing Sheets

| PSL DIAMETER [μm] | SCATTERING LIGHT QUANTITY |
|---|---|
| 0.0 | 1 |
| 0.1 | 40 |
| 0.2 | 500 |
| 0.3 | 1500 |
| 0.5 | 5000 |
| 0.8 | 55000 |
| 1.0 | 950000 |

FIG. 17

OPTICAL APPARATUS FOR DEFECT INSPECTION

BACKGROUND OF THE INVENTION

The present invention relates to a technology which can permit the detection accuracy in a defect detection optical apparatus to be corrected speedily and easily in order to optimize the aptness of geometrical dimension of defects and to suppress a variation in detection accuracy.

In semiconductor production process, if a foreign matter is present on a semiconductor substrate (wafer), it causes a defect such as faulty insulation or short-circuit of wiring to occur. With miniaturization of semiconductor devices advanced, even a minute foreign matter causes defective dielectric strength of capacitors or breakdown of gate oxide films. The foreign matter as above will be generated from moving components of a conveyance apparatus or from human bodies or through reactions with process gas in a processing apparatus or will mix with chemicals or materials, thus being supposed to mix in various conditions.

In one of techniques for detection of foreign matters on a wafer, a defect as represented by a foreign matter can be inspected by irradiating a laser beam on the wafer, detecting a ray of scattering light from the foreign matter or the like deposited on the wafer and comparing a result of inspection of the wafer with that of a wafer of the same kind inspected immediately precedently (see JP-A-62-89336).

SUMMARY OF THE INVENTION

In the optical apparatus for defect detection disclosed in JP-A-62-89336, optical conditions having the relation to an illuminating beam for inspection and lenses of a detection optical system as well vary with temperature, atmospheric pressure and time and the accuracy of detection of defects will sometimes change irregularly.

But the calibration curve used for conversion of the quantity of scattering light into to the size of a defect in the optical apparatus for defect inspection is prepared, in general, through a method in which the size of a defect measured actually by using an electron microscope in an inspection process of later stage of semiconductor production process, that is, a more reliable value is fed back to inspection data obtained with the optical defect inspection apparatus so as to be correlated with the quantity of scattering light. Accordingly, when trying to correct the measurement curve, much time is consumed before feedback of the result of measurement of the target defect portion with the electron microscope has been completed.

In addition, a line once operated typically continues running for a long period of time in the semiconductor production process and therefore, frequent check of the detection accuracy is difficult to achieve practically.

An object of the present invention is to provide an optical apparatus for defect inspection which can improve the system stability of semiconductor production line by speedily optimizing the aptness of defect geometrical dimension detection accuracy and suppressing a variation in detection accuracy.

(1) To accomplish the above object, according to the present invention, an optical apparatus for defect inspection having a stage for mounting a specimen, an illuminating optical system for irradiating illumination light beams for inspection having predetermined incident angles on the surface of the specimen to form a beam spot on the specimen surface and a detection optical system for detecting a reflection light ray originating from the beam spot, comprises a storage unit in which the position and size of a standard particle of known size arranged on a specimen for correction are stored in advance, a correction processing section which, when the specimen for correction is used as an inspection target, correlates an output from the detection optical system based on a scattering light ray from the standard particle of known size with the known size of standard particle stored at a corresponding position in the storage unit to prepare a correlation between the output of the detection optical system and a true value and a signal processing section which, when an inspection specimen is used as an inspection target, converts an output from the detection optical system into a size of a defect on the basis of the correlation prepared by the correction processing section.

(2) In the above (1), preferably, a specimens for calibration are sorted in accordance with their sizes and arranged in a plurality of areas which are predetermined in accordance with the sizes, and coordinates of the range of individual areas and sizes of standard particles arranged in the respective areas are stored in the storage unit.

(3) In the above (2), preferably, the plurality of areas for the correction specimens are arranged along a scan direction of the detection optical system.

(4) In the above (1), preferably, the detection optical system includes a TDI sensor as a detector and the correction processing section executes the procedure of correcting, in reference to one of a plurality of channels each having a plurality of one-dimensional sensors, the sensitivity levels of other channels.

(5) In the above (1), preferably, the detection optical system includes a TDI sensor as a detector and the correction processing section executes the procedure of correcting a sensitivity level of detection value obtained when scanning proceeds in one direction in reference to a detection value obtained when scanning proceeds in the other direction.

According to the present invention, since the detection accuracy can be corrected speedily and easily by only inspecting the specimen for correction, the aptness of accuracy of defect dimension detection can be optimized rapidly and variations in detection accuracy can be suppressed, thereby improving the system stability in the semiconductor production line.

Other objects, features and advantages of the invention will become apparent from the following description of the embodiments of the invention taken in conjunction with the accompanying drawings.

DESCRIPTION OF THE EMBODIMENTS

The present invention will now be described by way of example with reference to the accompanying drawings.

Figure 1:
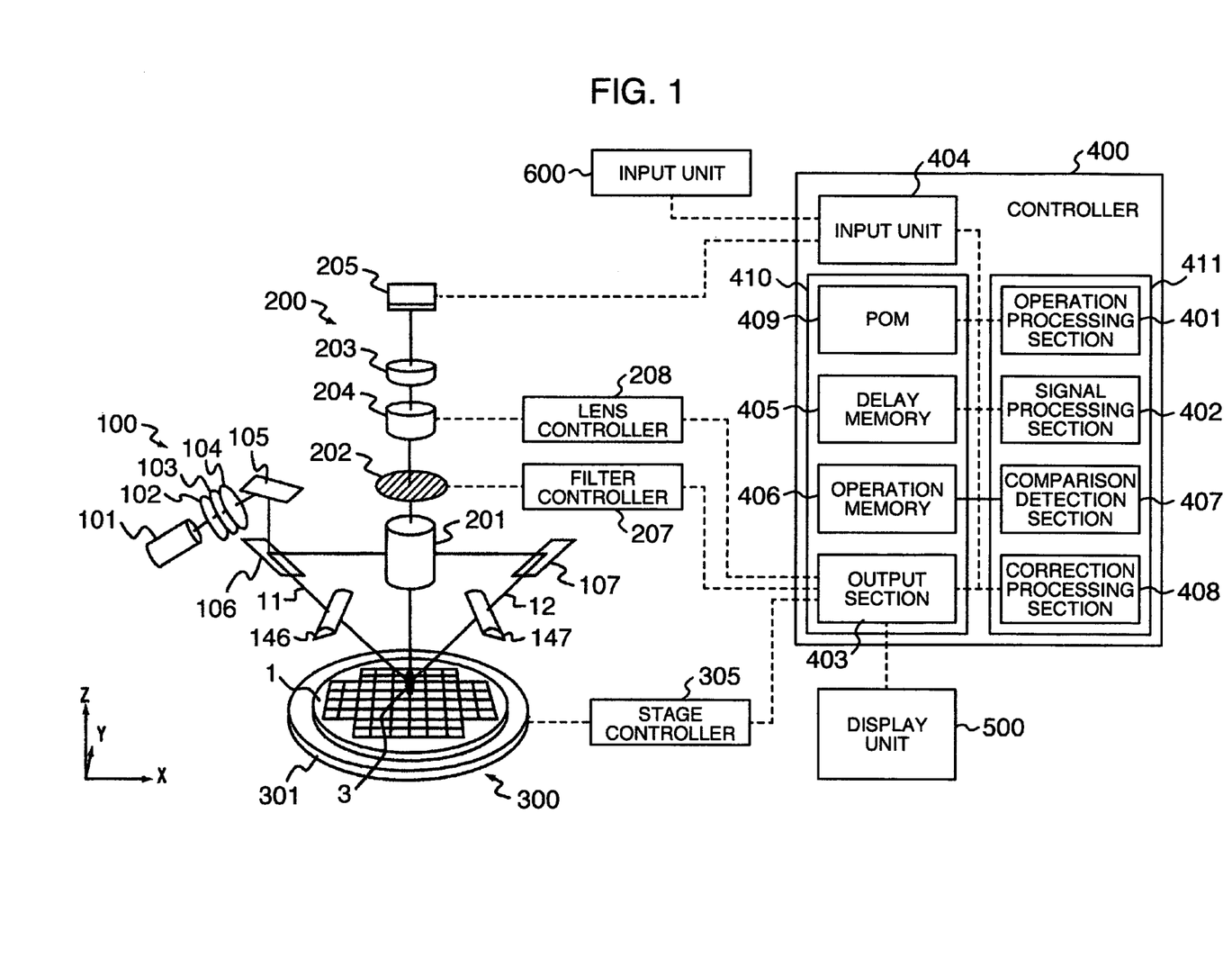
FIG. 1 is a diagram for explaining the construction of an optical apparatus for defect inspection according to an embodiment of the present invention.

Referring to FIG. 1, an optical apparatus for defect inspection according to an embodiment of the present invention is constructed as diagrammatically illustrated therein.

In FIG. 1, XY axes are defined on the horizontal plane and Z axis is defined upward vertically to the horizontal plane as indicated left below in the drawing. The Z axis passes through the center of a stage 301. The optical apparatus for defect inspection comprises a stage unit 300 having the function to move the stage 301 mounted with a specimen 1 such as a wafer along the respective axes in X, Y and Z directions and the function to rotate the stage 301 about the Z axis, an illuminating optical system 100 for irradiating light beams for inspection on the specimen 1, a detection optical system 200 for detecting a scattering light ray from the specimen 1, a controller 400 for performing an operation process and signal processing and the like and a display unit 500 for displaying results of detection on the basis of display signals from the controller 400.

Although not particularly illustrated, the stage unit 300 includes an X stage for moving the stage 301 in the X axis direction, a Y stage for moving the stage 301 in the Y axis direction, a Z stage for moving the stage 301 in the Z direction and a rotary stage for rotating the stage 301 about the Z axis and the individual stages perform corresponding operations to move the specimen 1. The stage unit 300 is connected with a stage controller 305 and the individual stages for moving the specimen 1 are operated by command signals from the stage controller 305.

The illuminating optical system 100 includes a laser light source 101, a beam expander comprised of a concave lens 102 and a convex lens 103, a beam shaper comprised of an optical filter group 104 and a mirror 105, a first beam spot image forming section having an optical branching element (or half mirror) 106 and a concave lens 146 and a second beam spot image forming section having a mirror 107 and a concave lens 147.

A preferred example of the laser light source 101 is a third harmonics generation (THG) high output YAG laser and preferably, its wavelength is about 355 nm. But the wavelength 355 nm is not a must. The laser light source 101 is not always a YAG/THG, either, and another type of light source such as an Ar laser, nitrogen laser, He—Cd laser or excimer laser may be used as the laser light source 101.

A laser beam emitted from the laser light source 101 is caused to branch to two optical paths by means of the optical branching element 106. One branching component is reflected by the mirror 107 so as to be incident on the concave lens 147, thus forming an illuminating light beam 12 for inspection to be delivered out of a second beam spot image forming section. The other branching component is incident on the concave lens 146, thus forming an illuminating light beam 11 for inspection to be delivered out of a first beam spot image forming section. These inspection illuminating light beams 11 and 12 irradiate the surface of specimen 1 obliquely while making predetermined angles to the normal of the specimen surface. Under the irradiation of inspection illuminating light beams 11 and 12, an elongate beam spot 3 is formed on the specimen 1.

The detection optical system 200 has a detection lens 201, a space filter 202, an image forming lens 203, a zoom lens group 204, a detector (image sensor) 205, a space filter controller 207 and a zoom lens controller 208. In the present embodiment, a TDI (time delay integration) sensor is used as the detector 205. An output signal from detector 205 is delivered to the controller 400. The optical axis of detection optical system 200 extends along the Z axis.

As soon as the inspection illuminating light beams are irradiated on the specimen 1 and the beam spot 3 is formed, a reflection beam including a scattering light ray is emitted from the specimen 1. The emission beam is given off from, for example, a defect such as foreign matter or a circuit pattern on the specimen 1. The emission beam passes through the detection lens 201, space filter 202 and image forming lens 203 and is received by the detector 205 where it undergoes photoelectric conversion. The intensity of illumination (power) of the laser beam from the laser light source 101 can be changed by controlling the space filter 202 or the laser power and therefore the dynamic range of the detector 205 can be changed.

The control system 400 includes an input unit 404 for receiving various kinds of signals, an operation unit 411 for performing various kinds of operation processes on the basis of various input signals, a storage unit 410 for storing input signals, operation results or constants or programs necessary for control and an output unit 403 for delivering signals to corresponding output destinations.

The storage unit 410 includes a ROM 409 for storing in advance programs and constants necessary for various operation processes and drive control, a delay memory 405 for temporarily storing operation results and the like and an operation memory 406 for storing correction coefficients and a size conversion table (both will be described later) which are necessary for processing detection signals from the detector 205.

The operation unit 411 includes an operation processing section 401 for operating various output signals, a signal processing section 402 for creating a detection image on the basis of the output from the detector 205, a comparison detection section 407 for detecting from the detection image a portion supposed to be a defect and a correction processing section 408 (to be described later) for correcting correction coefficients and conversion table stored in the operation memory 406.

The operation processing section 401 has a CPU (central processing unit) to execute the function to operate command signals to be outputted to the individual controllers 207, 208 and 305 and to the display unit 500 on the basis of input signals from an input unit 600 or programs. The respective command signals operated in the operation processing section 401 are outputted to the respective controllers 207, 208 and 305 and display unit 500 through the output unit 403, thus making it possible to control the operation of stage 301, the output of laser light source, the zoom magnification of zoom lens group 204 and the operation of space filter 202 or the focusing operation of a focus unit not shown and the display contents of display unit 500.

Figures 2A, 2B:
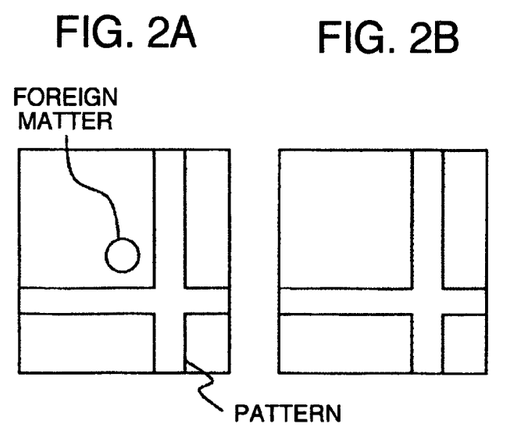
FIGS. 2A, 2B and 2C are diagrams illustrating defect detection images by a controller provided in the optical apparatus for defect inspection in the embodiment.

The signal processing section 402 creates a detection image (see FIG. 2A) of, for example, the surface of specimen 1 to be stored in the operation memory 406 on the basis of a digitized output from detector 205 delivered through the input unit 404. The thus created detection image is stored in the delay memory 405.

Figure 2C:
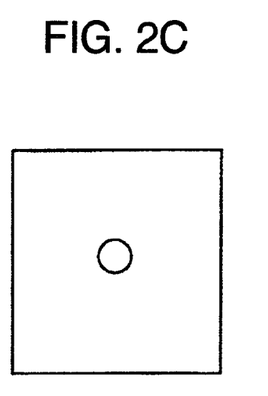

The comparison detection section 407 reads a detection image of adjacent chip (see FIG. 2B) stored in the delay memory 405 and compares it with the created inspection image (see FIG. 2A) to extract a signal difference so that a site where a difference in shape between adjoining chips exits may be detected. The comparison detection section 407 also creates a defect map (see FIG. 2C) by taking the detected difference site as data of a defect such as foreign matter or a defective pattern and stores the created data in a predetermined area of storage unit 410. Further, in order to properly evaluate the size of the specified defect, the comparison detection section 407 reads correction coefficients for TDI sensor (to be described later) from the operation memory 406 and corrects the output (scattering light quantity) from the detector 205. The corrected output value is then converted into a size of the defect in accordance with the size conversion table. The calculated defect size is stored at a predetermined area in the storage unit 410.

Figure 3:
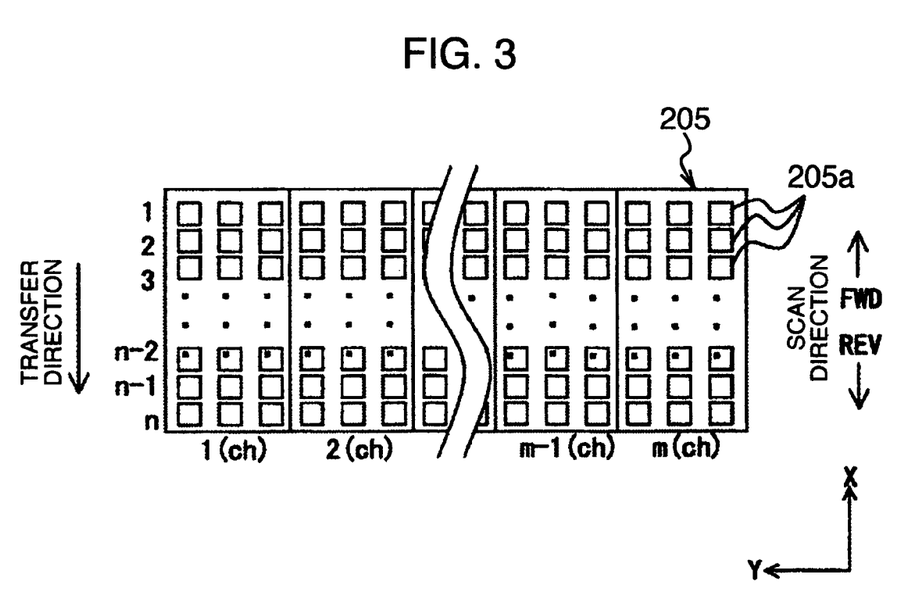
FIG. 3 is a diagram illustrating a detector provided in the optical apparatus for defect inspection in the embodiment.

It will now be understood that the TDI sensor used in the detection optical system 200 includes plural one-dimensional or linear sensors 205a arranged in multiple stages or rows (n stages or n rows) in the X axis direction (see FIG. 3). Through a method by which information of an image acquired with linear sensors 205 in the first stage is sequentially transferred to linear sensors 205a in the succeeding stage to integrate images, the quantity of light can be accumulated in accordance with the number of stages. In the case of this example, the detector 205 is formed having n stages arranged in the scanning direction (X axis direction) and m channels arranged in the Y axis direction, each channel being comprised of plural columns of linear sensors 205a (in FIG. 3, three columns are shown but the number of columns is not limitative).

In the present embodiment, the detector 205 can use not only a scattering light ray from the specimen when it moves relative to the specimen 1 in the positive X axis direction (FWD direction) but also a scattering light ray from the specimen 1 when it moves relative to the specimen 1 in the negative X axis direction (REV direction), in order to detect an image of the specimen 1. Then, in changing the scanning direction of the detector 205 from FWD direction to REV direction, the Y axis direction position of the detector 205 is moved by a predetermined distance upon direction change. This holds true for the case of direction change from REV direction to FWD direction. In other words, the detector 205 is moved in a zigzag fashion in relation to the specimen 1. In contrast, acquired information is transferred between adjacent stages of linear sensors 205a in only one direction toward the succeeding stage. In this case, the detection value becomes irregular in accordance with the scan direction (FWD/REV) but such an irregularity can be corrected through a method to be described later in the present embodiment.

Figure 4:
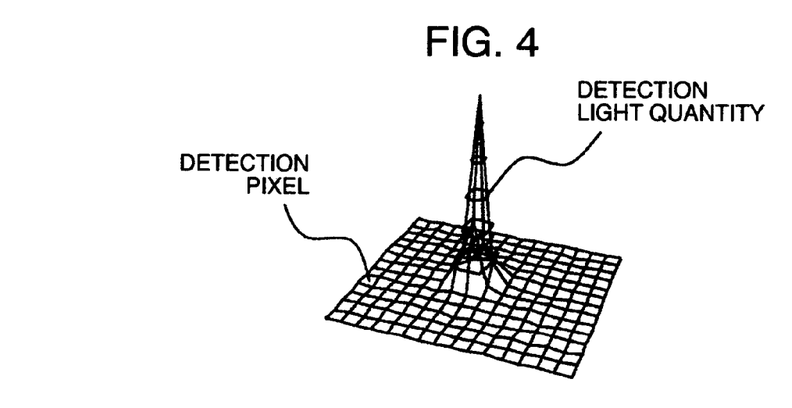
FIG. 4 is a diagram showing an image view of a detection scattering ray (within light reception capacity) detected by the detector provided in the optical apparatus for defect inspection in the embodiment.
Figure 5A:
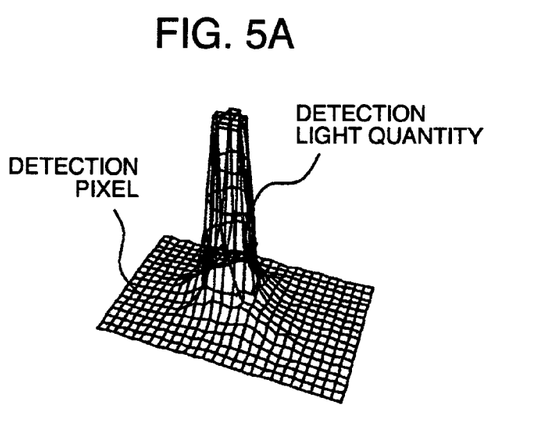
FIGS. 5A and 5B are diagrams useful to explain a correction image view of a detection scattering ray (in excess of light reception capacity) detected by the detector provided in the optical apparatus for defect inspection in the embodiment.
Figure 5B:
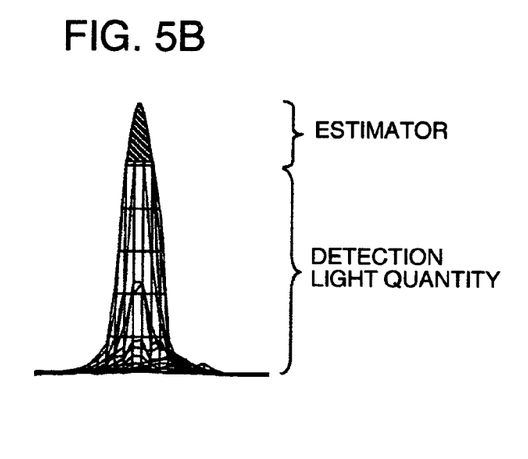

If in the present embodiment the quantity of reception light accumulated over the linear sensors 205a of first to n-th stages in each column is not saturated (see FIG. 4 for the case of the integrated value being within light reception capacity), it does not matter but if the integrated value of the quantity of reception light up to the n-th stage is saturated (see FIG. 5A for the case of the integrated value being in excess of light reception capacity), the quantity of scattering rays incident on the detector 205 cannot be grasped. To cope with this problem, in the present embodiment, an mathematical expression for light quantity estimation is stored in advance in, for example, the previously-described ROM 409 so that amounts in excess of the light reception capacity of sensor may be calculated by reading the expression as illustrated in FIG. 5B.

Figure 6:
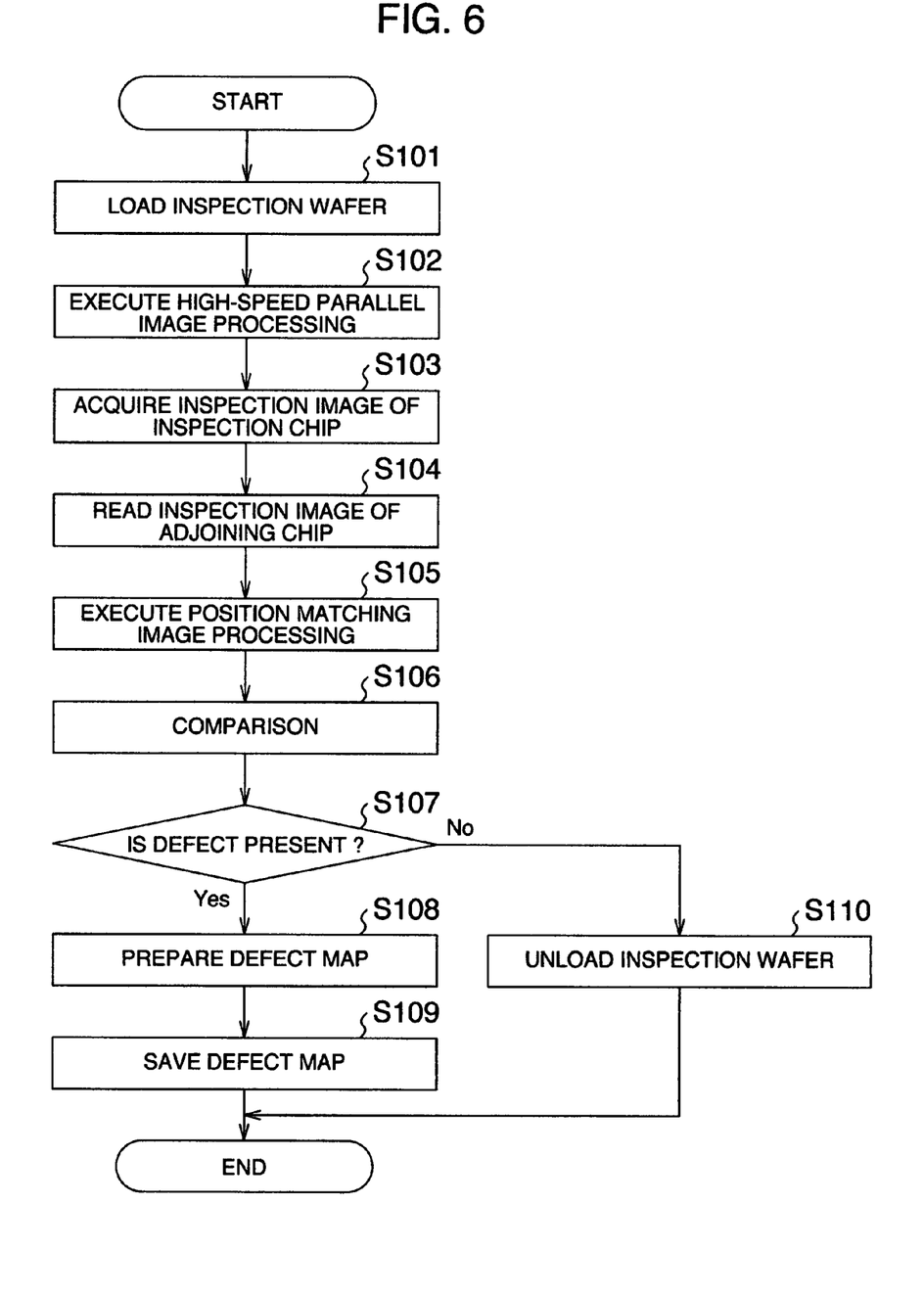
FIG. 6 is a flowchart showing the procedure of defect detection by the controller provided in the optical apparatus for defect inspection in the embodiment.

Turning now to FIG. 6, there is illustrated a flowchart showing the procedure of defect detection in the controller 400.

Firstly, when a specimen 1 (supposed to be an inspection wafer herein) set on the stage 301 is scanned (S101), the controller 400 receives an input signal from the detector 205 of detection optical system 200 through the input unit 404 and reads a program for signal processing from the ROM 409 to cause the signal processing section 402 to perform a high-speed parallel image processing of the input signal (S102), thus acquiring an inspection image (S103).

Subsequently, in S104, the comparison detection section 407 reads from the delay memory 405 an already acquired inspection image of an adjacent chip (standard chip) at a position corresponding to that of the inspection image acquired in the step S103 so that an image process for position matching between the acquired inspection image and the inspection image of adjacent chip may be carried out in S105. Then, the program proceeds to S106 where the acquired inspection image is compared with the inspection image of adjacent chip, followed by deciding the presence or absence of a defect from a comparison result (signal difference) in the ensuing S107.

If a defect is recognized in the step S107, the program proceeds to S108. In this step, on the basis of the defect detected through the detection optical system 200, the comparison detection section 407 specifies the position of the defect and prepares a defect map which in turn is stored at a predetermined area in the storage unit 410 (either the delay memory 405 or operation memory 406 may be usable for this purpose) in S109, ending the procedure of defect detection. On the other hand, when no defect is recognized in the step S107, the controller 400 proceeds to S110 where a command signal created in the operation processing section 401 is outputted to the stage controller 305 through the output unit 403 to unload the inspection wafer, ending the defect detection procedure.

In the optical apparatus for defect inspection adapted to inspect defects on the wafer surface, a defect map is prepared through the steps S108 and S109 in FIG. 6 and is utilized for a defect inspection process in the later stage carried out by an electron microscope (such as SEM). As the miniaturization of semiconductor devices advances, work to improve the inspection efficiency has been urgent and recently, even in the optical apparatus for defect inspection, improved accuracy and reliability of defect dimension detection has also been demanded.

In the optical apparatus for defect inspection, however, optical conditions having the relation to the illuminating light beam for inspection and lenses of detection optical system vary with temperature, atmospheric pressure and time. Irregularity in sensitivity of the sensor of detection optical system adds to the variation in the optical conditions to make the accuracy of detection of defect dimension liable to vary.

Typically, the measurement curve used for conversion of the quantity of scattering light into the size of a defect in the optical apparatus for defect detection is prepared through a method in which the size of a defect measured actually by using an electron microscope in an inspection process of later stage of semiconductor production process, that is, a more reliable value is fed back to inspection data obtained with the optical defect inspection apparatus so as to be correlated with the quantity of scattering light. Accordingly, when correcting the measurement curve, much time is consumed before feedback of the result of measurement of the target defect portion with the electron microscope has been completed.

In addition, a line once operated typically continues running for a long period of time in the semiconductor production process and therefore, frequent check of the detection accuracy is difficult to achieve practically.

Accordingly, in the present embodiment, with the aim of improving the system stability of semiconductor production line by speedily optimizing aptness of defect dimension detection accuracy and suppressing variations in detection accuracy, the function to be described below is provided.

Figure 7:
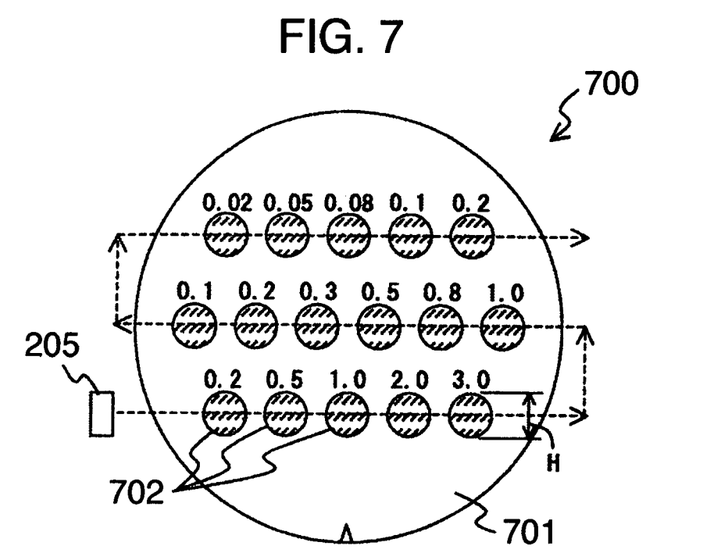
FIG. 7 is a diagram showing the schematic structure of a specimen for correction representing a tool for correction processing in the optical apparatus for defect inspection in the embodiment.

A specimen for correction is structured as illustrated in FIG. 7.

The specimen for correction 700 shown in FIG. 7 includes a wafer (substrate) 701 and a plurality of areas on the wafer in which lumps of foreign matters of known sizes (standard particles) sorted in size are arranged. Standard particle lumps coated in respective areas 702 are predetermined in connection with their size, number and interval. The sizes of individual standard particles to be disposed in the same area 702 are unified within a producible range but the size of a standard particle differs area by area. The size [µm] of a standard particle arranged in each area 702 is exemplified by a numerical value marked above the area. Preferably, each area 702 has its maximum dimension H in Y axis direction which is slightly smaller than the scan width per one scan by the detector 205 but the size and shape of the area 702 is not particularly limited.

Figure 8:
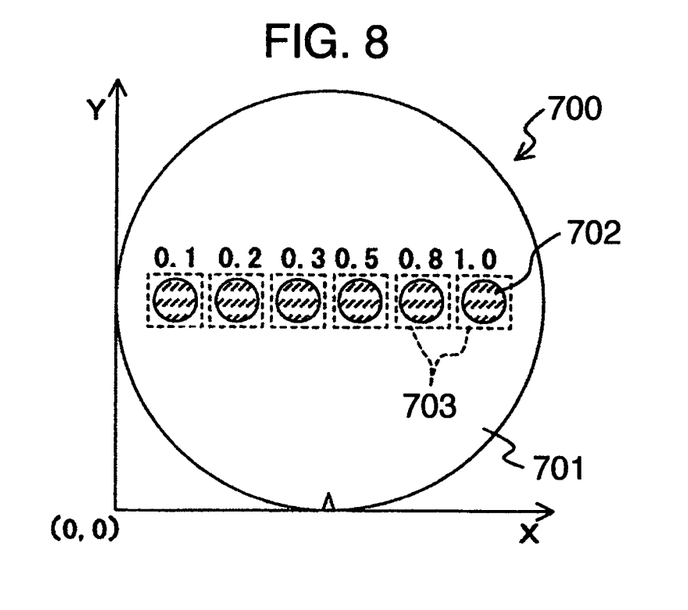
FIG. 8 is a diagram illustrating an example of a scan area for a correction specimen representing a tool for correction processing in the optical apparatus for defect inspection in the embodiment.

In the example shown in FIG. 7, the individual areas 702 are arrayed along the scan direction of detector 205 (in this example, X axis direction) and this arrangement is preferable for the purpose of efficiently scanning each area 702. And besides, plural columns of areas 702 are formed as necessary (an instance of three columns is illustrated in the present embodiment) and for the purpose of promoting efficiency, the locus of scan is so predetermined that the detector 205 passes over only the respective columns as indicated by dotted line in FIG. 7. Further, as shown in FIG. 8, more efficiency can be attained by permitting the detector 205 to scan only when it passes over the individual areas 702 and by forming the scan area intermittently as indicated by rectangular area 703. In FIG. 8, only one of three columns of areas 702 shown in FIG. 7 is extracted and illustrated.

In this instance, data of specimen for correction 700 as represented by the position of each area 702 (coordinates of area) and the size of a standard particle coated in each area 702 is stored in, for example, the previously-described ROM 409. If necessary, it is conceivable that for inspection of the correction specimen 700, the overall surface of the wafer is not scanned but a program for causing the operation processing section 401 to activate the detector 205 in such a way that the individual areas 702 can be scanned efficiently as described above may be stored in the ROM 409, for instance, apart from the program for inspection of the inspection wafer.

Then, by inspecting the correction specimen 700, the controller 400 can stabilize the accuracy of evaluation of the defect size, originating from the scattering light quantity, through the correction procedure to be described later which is executed by the correction processing section 408.

In executing the correction procedure, however, it is necessary for the controller 400 to recognize that the specimen for correction 700 is about to be inspected. To this end, various methods can be conceived and according to one of them, any inherent information, for example, is allotted in advance to the correction specimen 700 and when the inherent information is detected in the form of a detection signal from the detector 205, the controller 400 executes the correction procedure. In another method, when setting the correction specimen 700 on the stage 301, the user operates the input unit 600 so as to command the controller 400 to execute the correction procedure. Alternatively, it may be conceivable that a feed unit storing the correction specimen 700 apart from the inspection wafer is prepared separately, the correction specimen 700 can be set on the stage 301 by means of the feed unit in response to setting timing or a user's command and cooperatively therewith, the controller 400 can execute the correction procedure.

Figure 9:
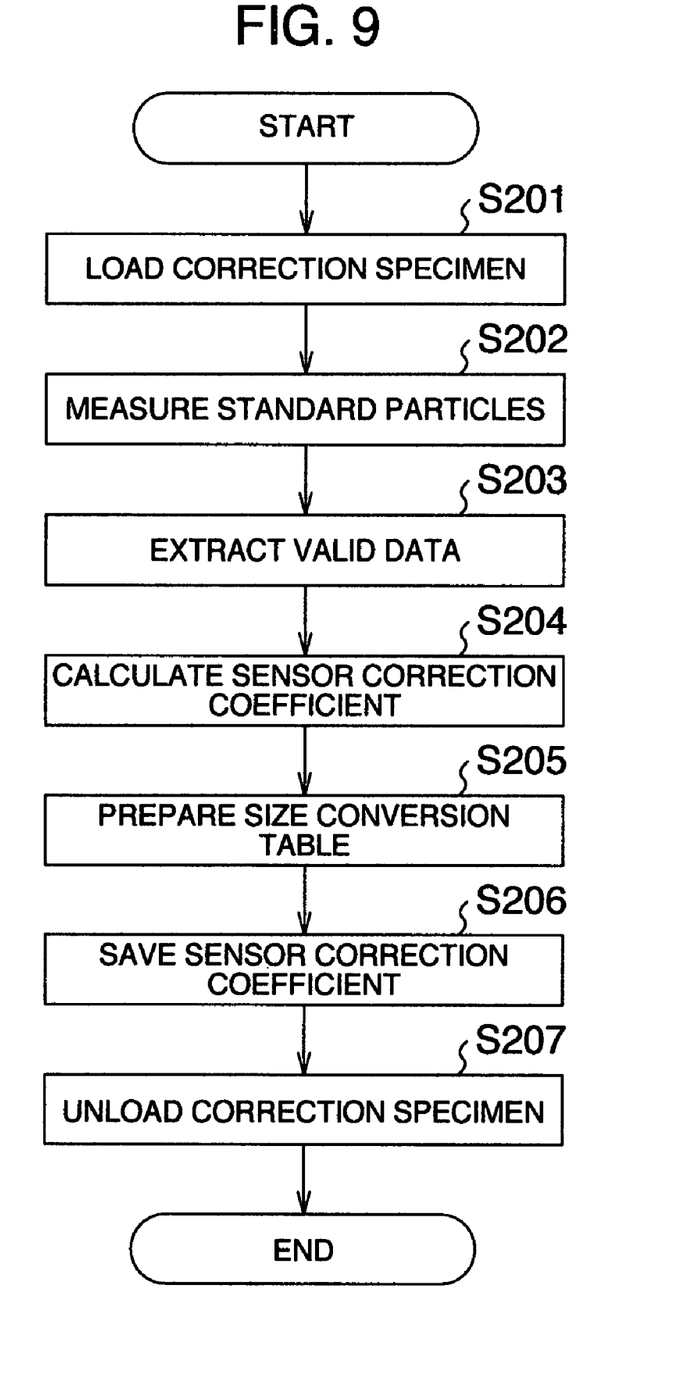
FIG. 9 is a flowchart showing the correction processing procedure by the controller provided in the optical apparatus for defect inspection in the embodiment.

Illustrated in FIG. 9 is a flowchart showing the correction processing procedure by the controller 400.

In FIG. 9, when a correction specimen 700 is loaded in S201, the controller 400 proceeds to the next step S202 and while the operation processing section 401 continues executing itself in accordance with a corresponding program stored in the ROM 409, the procedure of correction processing is started by the correction processing section 408. In the step S202, coordinate information of each area 702 stored in the ROM 409 is read to specify as to which standard particle area 702 a scattering ray originates from and whether the scattering ray is detected in the form of an output by the detector 205, the thus specified information is correlated with information in ROM 409 concerning the size of a standard particle (namely, true value) of the corresponding area 702 and the correlated information is saved in the operation memory 406.

As the program proceeds to S203, the controller 400 causes the correction processing section 408 to extract valid scattering light quantity data for the standard particles of individual areas 702. This procedure will be used later to correct detection values of respective channels of detector 205 for their irregularities.

Essentially, when standard particles of various sizes are arranged one by one on the wafer and the light quantity of scattering rays from individual standard particles is measured by shifting the detector 205 channel by channel, the scattering light quantity from one standard particle can be detected throughout the channels and the light quantities from the respective channels can be compared to one another. Actually, however, there is a possibility that foreign matter other than the standard particles (dust) is deposited irregularly on the wafer and a scattering light quantity from dust will be supposed to be measured erroneously as a scattering light quantity from a target standard particle.

In the present embodiment, the standard particles are coated in a lump inside a limited area 702 as has already been described and because of a distribution of the standard particles in the area 702, a portion of denser than ideal density and a portion of thinner than the ideal density are supposed to exist in the area 702. For example, at a highly dense portion of standard particles, scattering rays from plural standard particles (multi-scattering light ray) may be contained and they may be mistaken for a scattering light quantity from one standard particle, resulting in erroneous detection. In addition to the overlapping standard particles, plural proximate standard particles are responsible for scattering light quantities which are so affected by the optical proximity effect as to lack validity of data of scattering light quantity from one standard particle.

Figure 10:
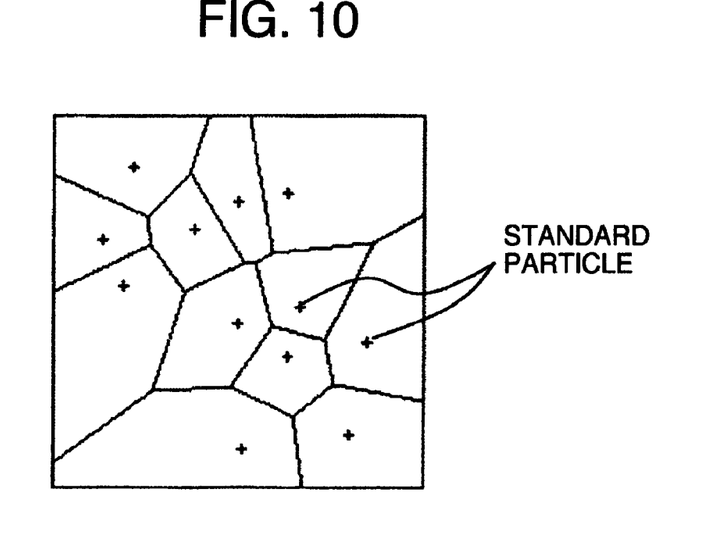
FIG. 10 is a Voronoi polygon diagram used in the correction processing procedure by the controller provided in the optical apparatus for defect inspection in the embodiment.
Figure 11:
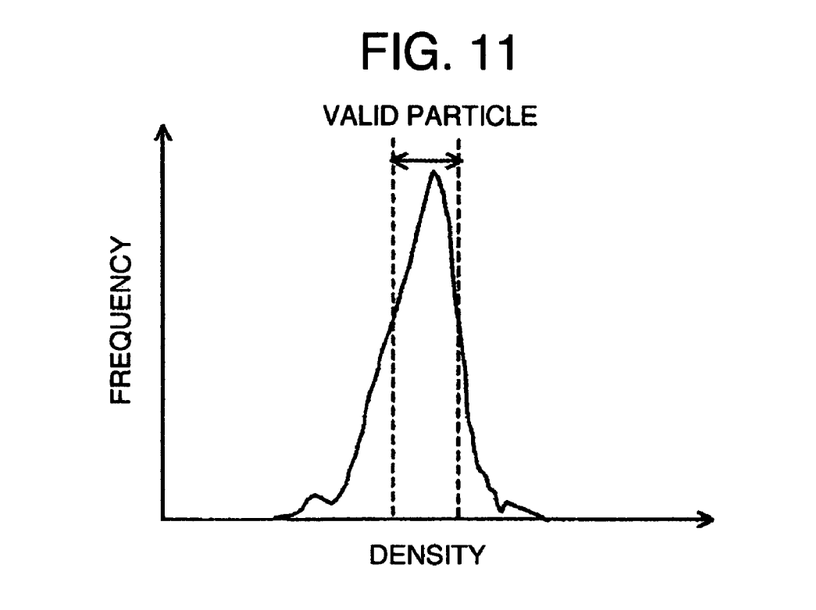
FIG. 11 is a graphic representation of valid data used for the correction processing procedure by the controller provided in the optical apparatus for defect inspection in the embodiment.

In the step S203, the controller 400 causes the correction processing section 408 to prepare a Voronoi polygon diagram (see FIG. 10) so as to calculate the density of standard particles on each area 702. Then, on the basis of the Voronoi polygon diagram, foreign matter having a thinner density than a designated distribution of standard particles and having a high possibility of being dust and proximate standard particles lacking validity of data as well are excluded and the remainder is defined as standard particles from which the scattering light quantity valid for detection value correction at each channel of the detector 205 can be obtained (valid particles) as shown in FIG. 11 and the scattering light quantity from the valid particle is detected as valid data. In a graph of FIG. 11, "frequency" on ordinate represents the number of standard particles existing in individual density ranges obtained by sectioning "density" on abscissa at equal intervals.

Next, in S204, the controller 400 causes the correction processing section 408 to correct the detection value for irregularities due to the channel and scan direction (FWD/REV) of the detector 205 as well in accordance with a predetermined program stored in the ROM 409.

Various factors including errors in diameter of a coated standard particle, uneven illumination of each of the illumination light beams 11 and 12 for inspection, uneven sensitivity of TDI sensor dependent on pixels, aberration of the detection optical system lens and color shading are responsible for irregularities of detection values based on channels, giving rise to a phenomenon that outputs acquired by measuring the same standard particle at respective channels are difficult to be identical to one another.

Figure 12:
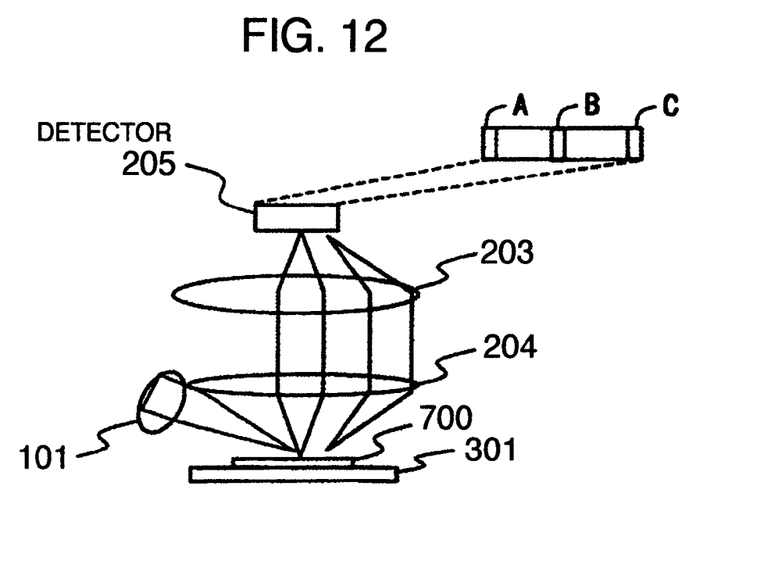
FIG. 12 is a diagram for explaining a method for correction of sensor sensitivity dependent on a sensor channel executed in the correction processing procedure by the controller provided in the optical apparatus for defect inspection in the embodiment.
Figure 13:
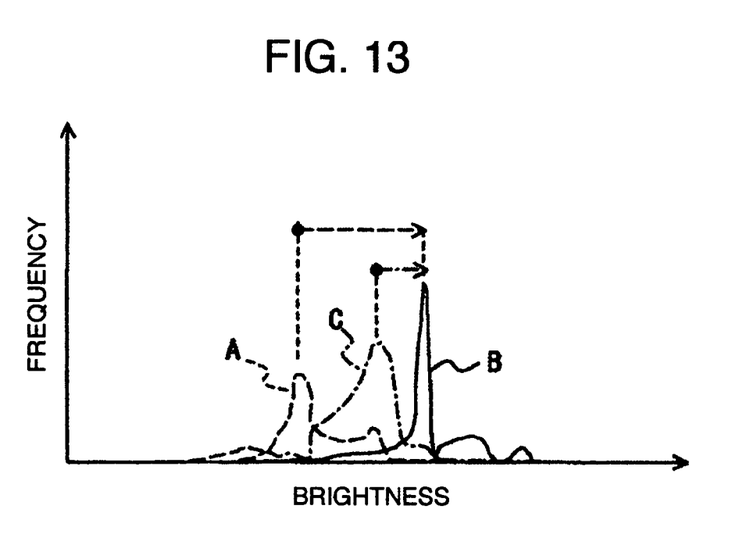
FIG. 13 is a graph showing an image view of correction of sensor sensitivity (correction coefficient) dependent on a sensor channel executed in the correction processing procedure by the controller provided in the optical apparatus for defect inspection in the embodiment.

Then, in the step S204, the center channel of detector 205 is taken as a criterion and channels around the reference channel are corrected. For example, when a channel B is positioned in the center of detector 205, channels at opposite ends, for example, among other channels are designated by A and C as shown in FIG. 12. In this case, detection light quantities at the channels A and C are converted into sensitive levels based on the detection light quantity of the reference channel B, so that irregularities in detection light quantities (illumination) due to the channels A, B and C can be corrected. It will be appreciated that the reference channel may not necessarily be the channel positioned in the center.

Specifically, where, for example, the scattering light detection quantity at the center channel B is Ib, scattering light detection quantities at channels A and C are Ia and Ic, respectively, correction coefficient Ka for channel A is defined as Ib/Ia and correction coefficient Kc for channel C is defined as Ib/Ic, the scattering light detection quantities from the channels A and C are multiplied by the correction coefficients Ka and Kc, respectively, thereby correcting the detection level for the channels A and C in terms of the detection level of the scattering light detection quantity from channel B. The correction referenced to the channel B can of course be applied similarly to other channels than the channels A and C.

Irregularity in detection value dependent on the scan direction is attributable to the difference in sensitivity of TDI sensor between the scan directions.

In correcting the irregularity in detection value dependent on the scan direction, an average value of valid data pieces of diameters the individual standard particles in lump have (different for areas 702) extracted in the S203 is calculated in the FWD and REV directions and the ratio between the both values is defined as a correction coefficient.

Figure 14:
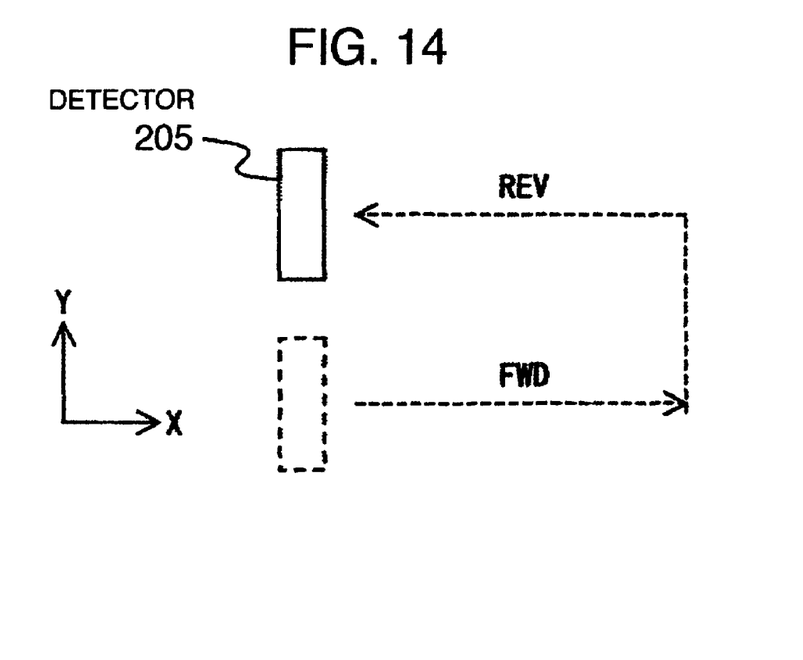
FIG. 14 is a diagram for explaining a method for setting sensor sensitivity dependent on scanning direction executed in the correction processing procedure by the controller provided in the optical apparatus for defect inspection in the embodiment.
Figure 15:
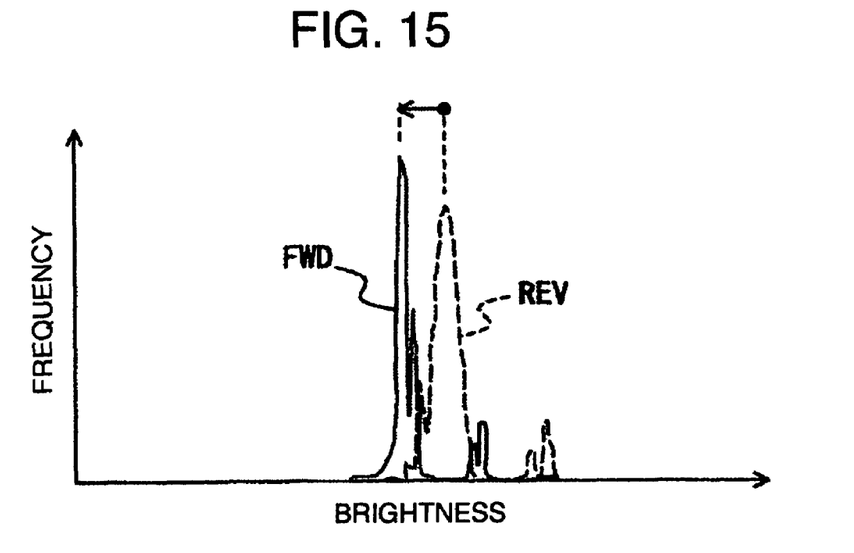
FIG. 15 is a graph of an image view of correction of sensor sensitivity (correction coefficient) dependent on scanning direction executed in the correction processing procedure by the controller provided in the optical apparatus for defect inspection in the embodiment.

More specifically, when in FIG. 14, for instance, the scattering light detection quantity during scanning in the FWD direction is Ifwd and the scattering light detection quantity during scanning in the REV direction is Irev, correction coefficient K is defined as Ifwd/Irev and the scattering light detection quantity during scanning in the REV direction at the time of inspection is multiplied by the correction coefficient K so that the detection level may be corrected in terms of the detection level of the scattering light detection quantity Ifwd during scanning in the FWD direction. In this case, the detection scattering ray during scanning in the FWD direction acts as the criterion and its detection value is not multiplied by the correction coefficient as shown in FIG. 15 but in some case the detection scattering light quantity during scanning in the REV direction may be used as a criterion.

Then, in the step S204, the detection scattering light quantity at channel A in FIG. 12 during scanning in the REV direction is multiplied by both the corresponding correction coefficient Ka(=Ib/Ia) and the scan direction correction coefficient K (=Ifwd/Irev), so that its detection level can be corrected in terms of the detection level when the center channel B is scanned in the REV direction.

Figure 16:
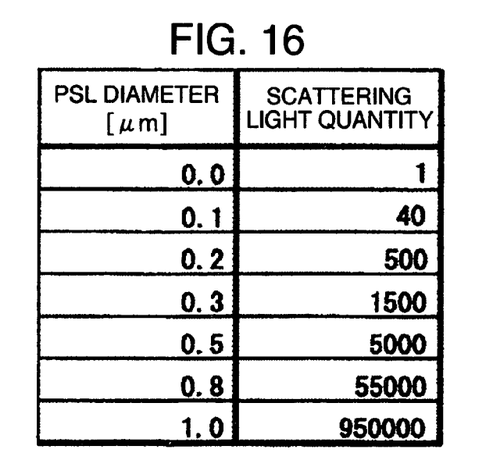
FIG. 16 is an exemplified size conversion table updated in the correction processing procedure by the controller provided in the optical apparatus for defect inspection in the embodiment.
Figure 17:
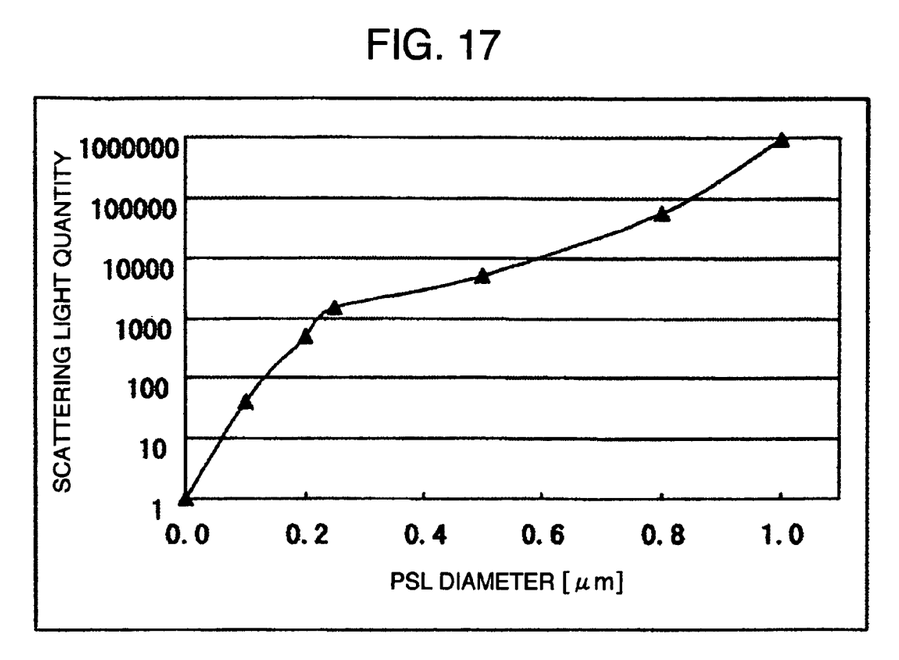
FIG. 17 is a graphic representation of a size conversion table updated through the correction processing procedure by the controller provided in the optical apparatus for defect inspection in the embodiment.

In the subsequent step S205, the controller 400 causes the correction processing section 408 to prepare a size conversion table (see FIG. 16) in which the standard detection scattering light quantity as a result of correcting the valid data extracted in the step S203 for its irregularity through the procedure of S204 is correlated with the corresponding standard particle size and the thus prepared table is stored in the operation memory 406. The size conversion table may be stored in the form of a graph as shown in FIG. 17 or a mathematic expression.

In the subsequent S206, the controller 400 then saves the correction coefficient calculated in the step S204 in the operation memory 406 and proceeds to S207 where the correction specimen 700 is unloaded and the present correction processing procedure ends.

Figure 18:
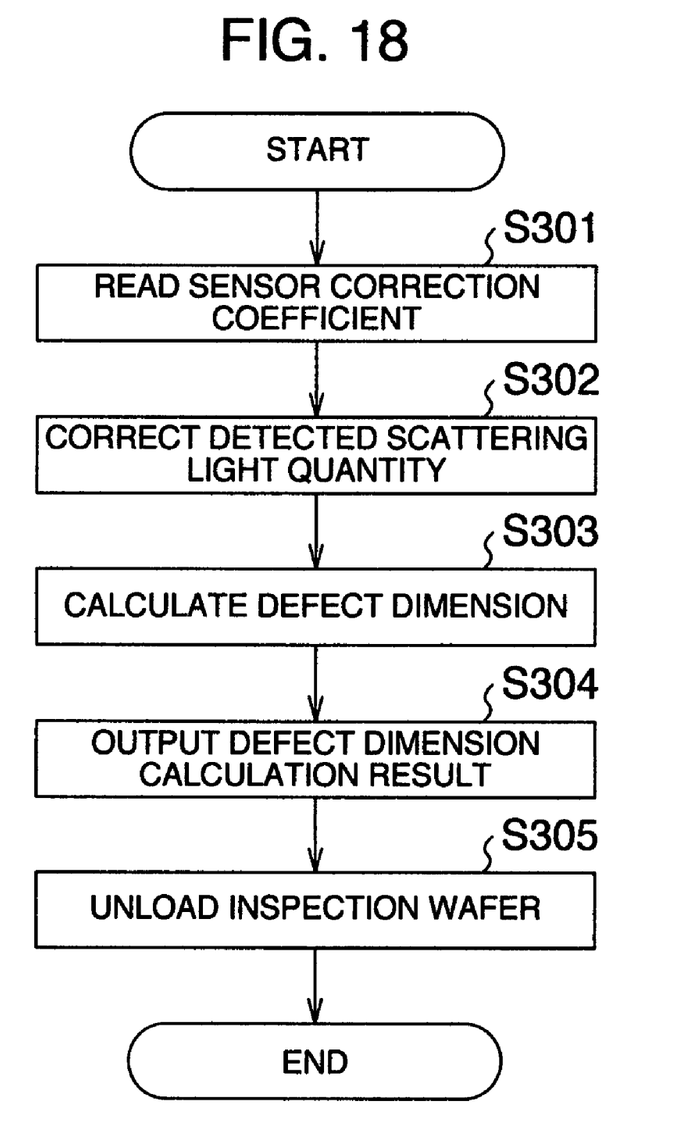
FIG. 18 is a flowchart showing the procedure of evaluating a geometrical dimension of a defect by the controller provided in the optical apparatus for defect inspection in the embodiment when the defect is recognized through inspection of an inspection wafer.

In case a defect is recognized through ordinary inspection of an inspection wafer, the controller 400 carries out the procedure for evaluation of defect dimension in accordance with a flowchart as illustrated in FIG. 18.

With a defect recognized in the step S107 of the defect detection procedure already described with reference to FIG. 6, the defect dimension is evaluated properly through the procedure shown in FIG. 18 by using the correction coefficients of the sensor structured as illustrated in FIG. 3 and the size conversion table on the basis of the defect information stored in the storage unit 410 in the step S109.

When a defect is recognized in the step S107 (see FIG. 6), the controller 400 starts the procedure in FIG. 18. Firstly, the controller reads the channel correction coefficient and scan direction correction coefficient stored in the operation memory 406 in the step S301 and causes the signal processing section 402 to use these correction coefficients properly so as to correct the detection scattering light quantity from the defective portion pursuant to the predetermined program in the ROM 409 (S302).

As the program proceeds to S303, the controller 400 reads the size conversion table from the operation memory 406 and causes the signal processing section 402 to convert the detection scattering light quantity evaluated properly in the step S302 into a defect dimension on the basis of the size conversion table. Then, in the next S304, the calculation result is outputted. In this case, the calculation result can be delivered to the display unit 500 and displayed thereon or delivered to a printer not shown. Needless to say, the calculation result can once be stored in the storage unit 410 or the like and can be outputted for display as desired by the user in accordance with operation of the input unit 600.

Lastly, in S305, the controller 400 outputs a command signal operated by the operation processing section 401 to the stage controller 305 to unload the inspection wafer, ending the defect dimension evaluation procedure.

As described above, the optical apparatus for defect inspection according to the present embodiment comprises the operation memory 406 for storing in advance the position (area) and size of standard particles on the correction specimen 700 and the correction processing section 408 for correlating, when the correction specimen 700 is used as an inspection target, an output of detector 205 based on a scattering light ray from a lump of standard particles with a known size of the standard particle stored at a corresponding position in the operation memory 406 to prepare a correlation between the output of detector 205 and a true value (size conversion table). Through this, by merely inspecting the correction specimen 700, irregularity of a detection result due to fluctuation of optical conditions can be corrected easily and automatically. In addition, since feedback of a result of another inspection step (inspection step by an SEM) is unneeded and the size conversion table can be updated from only the inspection result of the correction specimen 700, time required for accuracy correction can be decreased drastically. By executing the inspection of the correction specimen 700 at predetermined time intervals or automatically, the system stability of the semiconductor production line can be improved.

Further, in the present embodiment, the TDI sensor is used as the detector 205 and therefore, by calculating correction coefficients for correction of variations in detection value dependent on channels and variations in detection value dependent on the scan direction and by reflecting the calculation results upon the update of size conversion table and the defect dimension evaluation during inspection, higher reliability can be assured for the defect detection accuracy and the dimension evaluation accuracy.

Incidentally, with miniaturization of the semiconductor devices advanced in the recent years, the wavelength of the light source has become shorter and from the viewpoint of sensor sensitivity, many TDI sensors have been used. But, if the wavelength of the light source used can be detected highly accurately, the TDI sensor need not be used for the detector 205 and if structurally unnecessary, the channel correction coefficient need not be calculated. The present embodiment has been described by way of example of scanning the TDI sensor in both the FWD and REV directions but the present invention can also be applicable to the case where scanning is done in only one direction. In this case, the scan direction correction coefficient need not be calculated. The present invention is in no way limited to the foregoing embodiment but can obviously be changed or altered in various ways within the framework of the present invention as recited in the appended claims.

Further, all of the components in the storage unit 410 and operation processor 411 shown in FIG. 1 need not be provided in the controller 400 arranged integrally with the detection optical system 200. In other words, other types of storages can substitute for the memories such as the ROM 209, for example, and conceivably, they may be connected to the controller 400. As the case may be, part of the function the operation processor 411 has can be fulfilled with another computer connected to the controller 400. In this alteration, too, similar meritorious effects can be attained.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An optical apparatus for defect inspection having a stage for mounting a specimen, an illuminating optical system for irradiating illumination light beams for inspection having predetermined incident angles on the surface of the specimen to form a beam spot on the specimen surface and a detection optical system for detecting a reflection light ray originating from the beam spot, comprising:
   a storage unit in which the position and size of a standard particle of known size arranged on a specimen for correction are stored in advance;
   a correction processing section which, when the specimen for correction is used as an inspection target, correlates an output from said detection optical system based on a scattering light ray from the standard particle of known size with the known size of standard particle stored at a corresponding position in the storage unit to prepare a correlation between the output of said detection optical system and a true value; and
   a signal processing section which, when an inspection specimen is used as an inspection target, converts an output from said detection optical system into a size of a defect on the basis of the correlation prepared by said correction processing section.

2. An optical apparatus for defect inspection according to claim 1, wherein a plurality of specimens for correction are sorted in accordance with their sizes and arranged in a plurality of areas which are predetermined in accordance with the sizes, and coordinates of the range of individual areas and sizes of standard particles arranged in the respective areas are stored in said storage unit.

3. An optical apparatus for defect inspection according to claim 2, wherein said plurality of areas for the correction specimens are arranged along a scan direction of said detection optical system.

4. An optical apparatus for defect inspection according to claim 1, wherein said detection optical system includes a TDI sensor as a detector and said correction processing section executes the procedure of correcting, in reference to one of a plurality of channels each having a plurality of one-dimensional sensors, the sensitivity levels of other channels.

5. An optical apparatus for defect inspection according to claim 1, wherein said detection optical system includes a TDI sensor as a detector and said correction processing section executes the procedure of correcting a sensitivity level of detection value obtained when scanning proceeds in one direction in reference to a detection value obtained when scanning proceeds in the other direction.

* * * * *